(12) United States Patent
Waller et al.

(10) Patent No.: US 12,075,996 B2
(45) Date of Patent: *Sep. 3, 2024

(54) SOLENOID OCCLUSION DEVICE

(71) Applicant: University of Kansas, Lawrence, KS (US)

(72) Inventors: Stephen Clifford Waller, Overland Park, KS (US); Alyssa Kirk Burke, Lawrence, KS (US); Richard Kevin Gilroy, Fairway, KS (US); Philip Lee Johnson, Overland Park, KS (US); James Marion Stiles, Prairie Village, KS (US); Sara Ellen Wilson, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 778 days.

This patent is subject to a terminal disclaimer.

(21) Appl. No.: 17/085,870

(22) Filed: Oct. 30, 2020

(65) Prior Publication Data

US 2021/0068797 A1 Mar. 11, 2021

Related U.S. Application Data

(63) Continuation-in-part of application No. 16/804,909, filed on Feb. 28, 2020, now Pat. No. 11,478,236.
(Continued)

(51) Int. Cl.
*A61B 17/00* (2006.01)

(52) U.S. Cl.
CPC .... *A61B 17/0057* (2013.01); *A61B 17/00491* (2013.01); *A61B 2017/00292* (2013.01);
(Continued)

(58) Field of Classification Search
CPC .......... A61B 17/0057; A61B 17/00491; A61B 17/12022; A61B 17/12186; A61B 17/12195; A61B 17/12181; A61B 2017/00292; A61B 2017/00641; A61B 2017/0065; A61B 2017/00951; A61N 2/02; A61M 2037/0007
See application file for complete search history.

(56) References Cited

U.S. PATENT DOCUMENTS

| | | | |
|---|---|---|---|
| 7,218,962 B2 * | 5/2007 | Freyman | A61N 2/002 604/93.01 |
| 8,900,293 B2 * | 12/2014 | Forbes | A61F 2/82 607/9 |

(Continued)

*Primary Examiner* — Diane D Yabut
(74) *Attorney, Agent, or Firm* — RAY QUINNEY & NEBEKER P.C.; Paul N. Taylor

(57) ABSTRACT

The present disclosure relates to devices and methods for delivery of a ferrofluid to a targeted treatment site, such as delivery of a ferroadhesive to a pathological fistula to occlude the fistula. A device includes a catheter having a lumen and a distal opening. A hollow solenoid is coupled to a distal section of the catheter, and a hollow core of the solenoid allows passage of a ferrofluid through the catheter and through the hollow core so that it may exit past the distal end of the hollow solenoid. The solenoid may be selectively actuated to maintain or control the position of the delivered ferrofluid.

20 Claims, 13 Drawing Sheets

Related U.S. Application Data which is a continuation of application No. 15/419,296, filed on Jan. 30, 2017, now Pat. No. 10,575,839, which is a continuation-in-part of application No. PCT/US2015/042601, filed on Jul. 29, 2015.

(60) Provisional application No. 62/402,117, filed on Sep. 30, 2016, provisional application No. 62/030,458, filed on Jul. 29, 2014.

(52) U.S. Cl.
CPC ............... *A61B 2017/00544* (2013.01); *A61B 2017/00641* (2013.01); *A61B 2017/0065* (2013.01); *A61B 2017/00876* (2013.01); *A61B 2017/00951* (2013.01)

(56) References Cited

U.S. PATENT DOCUMENTS

2002/0087177 A1\* 7/2002 Wallace ........... A61B 17/12186
 606/157
2008/0105700 A1\* 5/2008 Voegele ........... A61B 17/00491
 222/395

\* cited by examiner

SOLENOID OCCLUSION DEVICE

CROSS-REFERENCE TO RELATED APPLICATIONS

This application is a continuation-in-part of U.S. application Ser. No. 16/804,909, filed Feb. 28, 2020, which is a continuation of U.S. application Ser. No. 15/419,296, filed Jan. 30, 2017, now U.S. Pat. No. 10,575,839, which is a continuation-in-part of PCT Application Serial No. PCT/US2015/042601, filed Jul. 29, 2015, which claims priority to and the benefit of U.S. Provisional Patent Application Ser. No. 62/030,458, filed Jul. 29, 2014. U.S. application Ser. No. 15/419,296 also claims priority to and the benefit of U.S. Provisional Patent Application Ser. No. 62/402,117, filed Sep. 30, 2016, the entireties of which are incorporated herein by reference.

BACKGROUND

Fistulas are abnormal tunnels between two tissues within the body. These pathogenic ducts can lead to health problems if left untreated. They commonly occur in the gastrointestinal tract as well as biliary conduits, and can also be seen in the vascular system. If left untreated, fistulas can cause abscesses, infections and other complications. Typically, a fistula that is unable to heal or which develops abscesses, infections, or other complications requires treatment through an invasive surgical procedure. Currently, fistula treatment requires extensive surgery under general anesthesia, followed by several weeks of recuperation. Such procedures are also typically associated with high patient costs. Further, some patients have poor health conditions and are poor candidates for such surgeries in the first place.

Various forms of glues have been explored for use in less invasive tissue closure methods. Cyanoacrylates are the compounds most commonly used for these purposes. These compounds are generally liquid monomers that polymerize into longer polymer chains upon exposure to moisture. There are several varieties designed for medical use in humans. Problems in using these compounds to treat a fistula arise from the difficulty in maintaining precise control of the glue. In some circumstances, the glue can flow away from the targeted treatment site before setting, which risks damaging, obstructing, or occluding non-targeted tissues or anatomical structures. Likewise, the glue delivery device can become entrapped against or within the treatment site if the glue is injected too slowly relative to the polymerization rate of the glue.

BRIEF SUMMARY

Certain embodiments described herein are directed to a delivery device including a catheter having a lumen extending to a distal opening. The device also includes a solenoid coupled to the catheter at a distal section of the catheter. The solenoid has a hollow core such that the catheter can extend into the hollow core or otherwise connect to the hollow core to allow passage of a ferrofluid through the catheter, through the solenoid, and distally past the delivery device to a targeted treatment site. The solenoid also includes an electrically conductive coil disposed around at least a portion of an outer circumferential surface of the core. The solenoid is configured to selectively provide a magnetic field having strength sufficient to hold or otherwise control a bolus of the ferrofluid at a desired treatment site.

In certain embodiments, a delivery device is configured for delivering a ferroadhesive to a targeted pathological fistula in order to occlude the fistula. The delivery device includes a catheter having a lumen extending to a distal opening. A solenoid is coupled to the catheter at a distal section of the catheter. The catheter extends at least partially into a hollow core of the solenoid so that a ferroadhesive may be delivered through the catheter, through the hollow core, and past the delivery device to the targeted fistula. The solenoid is configured to selectively provide a magnetic field having strength sufficient to hold a bolus of the ferroadhesive at the targeted fistula until the ferroadhesive has sufficiently set.

Certain embodiments are directed to a method of delivering a ferrofluid to a targeted treatment site. The method includes positioning a distal end of a delivery occlusion device near the targeted treatment site, delivering an amount of a ferrofluid through a catheter of the delivery device and past a distal opening of the delivery device to the targeted treatment site, and actuating a solenoid of the device to generate a magnetic field to hold at least a portion of the ferrofluid at the targeted treatment site. In some embodiments, the targeted treatment site is a pathological fistula, and the ferrofluid is a ferroadhesive. In some embodiments, the method includes maintaining position of the delivered ferroadhesive at the fistula until the ferroadhesive has sufficiently solidified.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

One or more embodiments described herein relate to devices configured for forming an occlusion at a targeted treatment site within a body, such as to plug a pathological fistula. At least some of the embodiments disclosed herein include a catheter having an interior lumen extending to a distal opening at the distal end of the catheter. A distal section of the catheter is configured as a solenoid operable to selectively generate a magnetic field at the vicinity of the distal section of the catheter. In certain implementations, the generated magnetic field provides control over a bolus of magnetically responsive adhesive delivered through the lumen of the catheter and exiting out of the distal opening of the catheter. Beneficially, in some embodiments, the solenoid is configured as a hollow solenoid disposed in mechanical relationship with the catheter so as to allow use of the catheter for the delivery of occlusion-forming adhesive materials and other materials. Alternatively, a solenoid having a solid core is disposed within a catheter so as to provide inter-luminal space between the outer diameter of the solenoid and the inner diameter of the catheter to enable the delivery of a ferroadhesive through the inter-luminal space. One or more embodiments described herein therefore enable positional control of a delivered bolus of tissue adhesive, thereby providing more effective treatment of pathological fistulae.

Embodiments of the present disclosure may be configured for use in a variety of treatment settings. For example, the device and methods may be used in the closure of fistulas (such as enterocutaneous, biliary, rectovaginal, enterovesicle, enterourethral, esophageal, etc.), in the treatment of biliary or pancreatic duct leaks, and in the treatment of gastric varices, ateriovenous malformations, and vascular aneurysms. In particular, aspects of the present disclosure are directed to occlusion devices and methods of forming occlusions that allow precise locational control of a bolus of occlusion-forming material (e.g., glue/adhesive). In at least some embodiments, the occlusion device is configured to be detachable and extractable from a forming or formed occlusion without disrupting the occlusion or surrounding tissues or structures.

Although many of the exemplary embodiments are described herein in the context of delivering an adhesive or glue material for forming an occlusion to treat a fistula, it will be understood that the principles described herein may also be applied in other uses or treatment contexts. For example, described features may be applied generally to other treatment contexts involving the controlled delivery of a ferrofluid (adhesive or non-adhesive) to a treatment site (fistula or non-fistula).

Figure 1A:
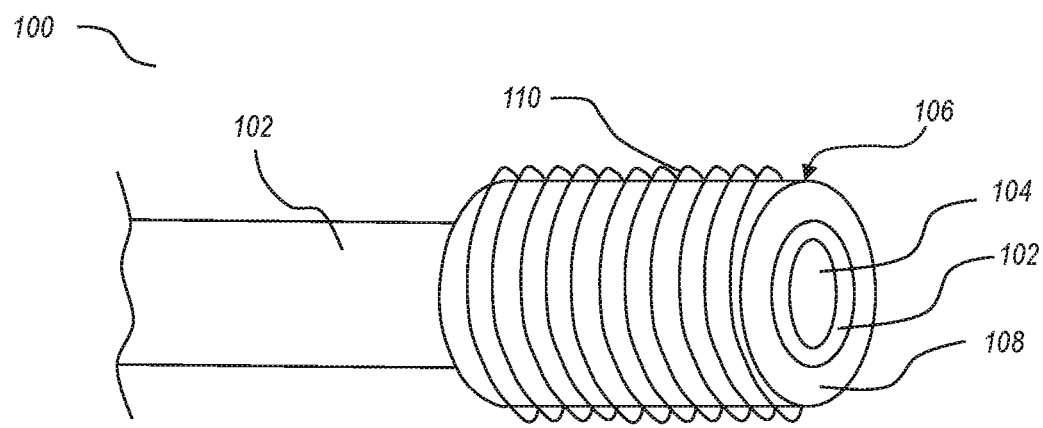
FIG. 1A illustrates an embodiment of a hollow solenoid delivery device configured to deliver a ferrofluid.

FIG. 1A illustrates an embodiment of an occlusion device 100 configured to enable delivery of and positional control over an occlusion-forming tissue adhesive. As shown, the occlusion device 100 includes a catheter 102. The catheter 102 includes an interior lumen extending to a distal opening 104. A distal section of the catheter 100 includes components and features enabling the distal section to function as a solenoid 106. As shown, the solenoid 106 includes a core 108 and a coil 110 surrounding the core 108. In some embodiments, the coil 110 is coupled to one or more leads (not shown) extending proximally from the solenoid 106 to a power supply for supplying power to the solenoid 106 (e.g., any source of sufficient power, such as a battery powered supply and/or a connection to a wall outlet). For example, the one or more leads may extend through one or more lumens provided within the catheter 102.

In the illustrated embodiment, the solenoid 106 is configured with a hollow structure so as to provide an interior lumen through which the catheter 102 may at least partially extend or through which the lumen of the catheter 102 may join. The hollow structure of the solenoid 106 thereby enables fluid (e.g., a ferrofluid and/or other materials) to be delivered through the catheter 102, through the solenoid 106, and through the distal opening 104 to a targeted area distal from the solenoid 106 and distal opening 104.

In the illustrated embodiment, the solenoid 106 is configured to, upon receiving electrical current, generate a magnetic field for influencing the positioning of a magnetically-responsive material, such as a magnetically-responsive tissue adhesive delivered through the catheter 102. The generated magnetic field can function to maintain the location of the adhesive. For example, the generated magnetic field provided by the activated solenoid 106 can prevent the adhesive material from locating to and/or adhering to undesired areas, such as adjacent ducts and vascular structures. The illustrated solenoid 106 may therefore function as an electromagnet capable of being selectively activated and deactivated in response to application of electrical current. In addition, the strength of the generated magnetic field may be manipulated by adjusting the current and/or voltage supplied to the solenoid 106. In at least some implementations, this beneficially enables fine-tuned control over the positional manipulation of a bolus of magnetically responsive adhesive.

In embodiments described herein, the term "catheter" is used to denote a structure having one or more lumens and that is suitable for routing to a targeted anatomical treatment site, such as a pathological fistula. Catheters may have any size suitable for a desired application. For example, catheters may have an inner diameter or an outer diameter within a range of 3 to 34 Fr, or about 5 to 26 Fr. The catheters described herein may be used in conjunction with an endoscope system (e.g., with a distally positioned camera), such as for use as a colonoscope in an enterocutaneous fistula repair procedure. One or more embodiments described herein may also be used in conjunction with imaging modalities to aid in proper positioning of the occlusion device. For example, an occlusion device may be utilized in conjunction with X-ray, fluoroscopy, ultrasound, infrared, other imaging modalities, or combinations thereof.

As used herein, the terms "magnetically responsive fluid," "magnetically responsive adhesive," "magnetically responsive glue," and the like refer to substances that are deliverable to a targeted treatment site and which are capable of being positionally manipulated in response to an imparted magnetic field. The term "ferrofluid" is used herein to refer to a magnetically responsive fluid formed as a suspension of ferrous particles (e.g., nano- or micro-sized) within a carrier. A ferrofluid includes particles sized such that Brownian motion of the particles prevents particle alignment and allows the ferrofluid to function as a paramagnetic material (i.e., a material that only maintains a magnetic moment during exposure to a magnetic field).

In some embodiments, a ferrofluid includes a suspension of particles where the particles have an average particle diameter of about 5 to 15 nm, or about 8 to 12 nm. In some embodiments, the ferrous particles are suspended along with a surfactant, such as an anionic surfactant. In some embodiments, the ferrofluid includes ferroparticles at a concentration of about 0.1 to 3 g/ml, about 0.5 to 2 g/ml, about 0.75 to 1.5 g/ml, or about 1.3 g/ml. One exemplary ferrofluid, which is available under the trade name EMG 700, includes ferroparticles having a nominal particle diameter of about 10 nm, included at a concentration of about 1.29 g/ml suspended in water along with an anionic surfactant. The ferrofluid may be combined with water, saline, other fluids, or combinations thereof according to particular application needs.

As used, herein, the term "ferroadhesive" refers to a particular type of ferrofluid including ferrous nanoparticles suspended within an adhesive carrier material. For example, the adhesive carrier can include a biocompatible cyanoacrylate material, fibrin glue, other adhesive suitable for medical or surgical use, or combinations thereof. By way of another example, a ferrofluid may be blended with a suitable adhesive to form the ferroadhesive. In some embodiments, the ferrofluid is included, by weight of the resulting ferroadhesive, at about 10, 20, 30, 40, 50, 60, 70, 80, or 90%, or at a concentration within a range having endpoints defined by any two of the foregoing values. Although particular examples described herein may refer specifically to ferroadhesive or other particular type of magnetically responsive material, it will be understood that the alternative embodiments may substitute the ferroadhesive for other magnetically responsive materials that are known in the art or which may be discovered.

In the embodiment illustrated in FIG. 1A, the core 108 encompasses the distal section of the catheter 102. The core 108 is preferably formed from one or more materials providing high magnetic permeability. Presently preferred embodiments include iron. Alternative embodiments may include metallic glass, mu-metal, cobalt-iron alloys, nickel-iron alloys (e.g., permalloy), ferritic stainless steel, martensitic stainless steel, magnetically permeable ceramics (e.g., ferrite), or combinations thereof.

In some embodiments, the core 108 is formed as a solid integral piece of material. In other embodiments, the core 108 includes separate sections, such as a laminate structure of multiple layers. For example, as explained in more detail below, some embodiments include a core formed from one or more layers of wire (e.g., formed in a coil around a catheter) coated with a paint to fill in interstitial gaps between adjacent sections/coils of the wire. The wire and/or paint are preferably formed from one or more of the highly permeable materials described herein (e.g., iron). Subsequent examples refer particularly to iron wire and iron paint embodiments. However, it will be understood that in alternative embodiments, the wire and/or paint components may include one or more of the alternative highly magnetically permeable materials described herein.

The solenoid 106 may be provided with a longitudinal length tailored for a particular application or set of applications. In some embodiments, the solenoid has a length of about 0.5 cm, 1 cm, 2 cm, 3, cm, 4 cm, 5 cm, or a length within a range defined by any two of the foregoing values. For example, beneficial results have been shown using a solenoid 106 having a length within a range of about 1 to 3 cm.

In the illustrated embodiment, the inner diameter of the hollow solenoid 106 is defined by the catheter 102 to which the core 108 of the solenoid 106 encompasses. The inner diameter may be configured to suit a particular application or set of applications. In at least some embodiments, the inner diameter measures about 0.5 mm, 0.75 mm, 1 mm, 1.5 mm, 2 mm, 3 mm, 5 mm, 10 mm, 15 mm, or measures within a range defined by any two of the foregoing values. For example, beneficial results have been shown using a device having an inner diameter of about 1 mm.

In the illustrated embodiment, the outer diameter of the hollow solenoid is defined at least in part by the thickness of the core 108 and the thickness of the coil 110. The outer diameter may be configured to suit a particular application or set of applications. In at least some embodiments, the outer diameter measures about 1 mm, 1.5 mm, 2 mm, 3 mm, 5 mm, 10 mm, 15 mm, 18 mm, or measures within a range defined by any two of the foregoing values. For example, beneficial results have been shown using a device having an outer diameter of about 1.5 to 4 mm.

The coil 110 may be formed from one or more electrically conductive materials, such as copper, gold, silver, other conductive materials, or combinations thereof. In some embodiments, the coil 110 is formed from a wire material having a diameter measuring about 0.08 mm, 0.1 mm, 0.14 mm, 0.18 mm, 0.25 mm, 0.4 mm, 0.7 mm, 1 mm, or measuring within a range defined by any two of the foregoing values. For example, beneficial results have been shown using a coil made from wire having a diameter within a range of about 0.33 mm to 0.66 mm. The coil 110 may be wrapped around the core 108 by an amount necessary for a particular application or set of applications. In some embodiments, the coil is wrapped around the core 110 to provide a turns per unit length value (where unit length refers to longitudinal length of the core 108) of about 5 turns/cm, 10 turns/cm, 20 turns/cm, 40 turns/cm, 60 turns/cm, 100 turns/cm or a turns per unit length measurement within a range defined by any two of the foregoing values. For example, beneficial results have been shown using a turns per unit length value of about 15 to 20 turns/cm.

Figure 1B:
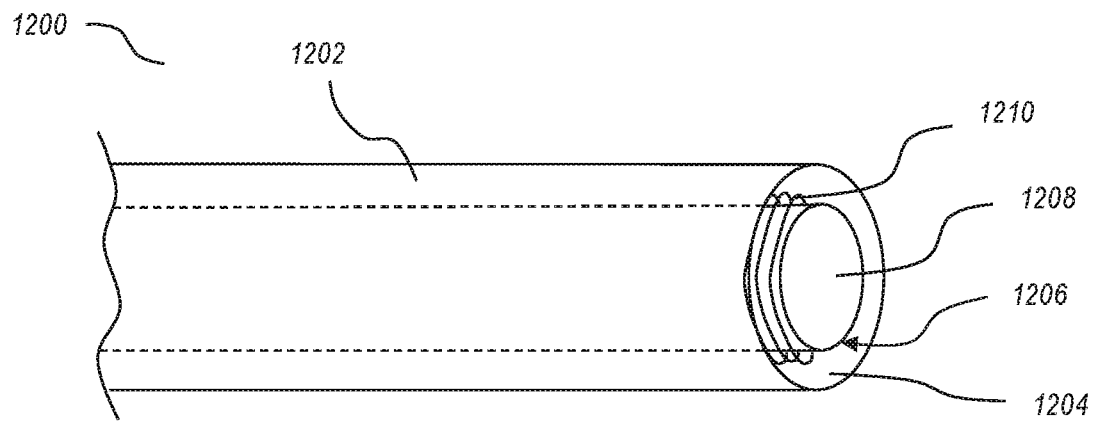
FIG. 1B illustrates another embodiment of a solenoid delivery device having a solid core solenoid disposed within a catheter configured to deliver a ferrofluid.

FIG. 1B illustrates an alternative embodiment of an occlusion device 1200 in which a solenoid 1206 is disposed within a catheter 1202 in a manner so as to define an inter-luminal space between the outer diameter of the solenoid 1206 and the inner wall of the catheter 1202. The illustrated embodiment may otherwise be configured similar to the embodiment of FIG. 1A (with respect to material selection, sizes, operational characteristics, etc.). In this embodiment, the solenoid core 1208 is formed as a solid component, and the coil 1210 wrapped around the core 1208 is also disposed within the inter-luminal space. In operation, rather than passing a ferrofluid through a lumen within the solenoid, as with the embodiment of FIG. 1A, the fluid may be passed through the inter-luminal space between the catheter 1202 and the solenoid 1206 and through the distal opening 1204.

Figure 2A:
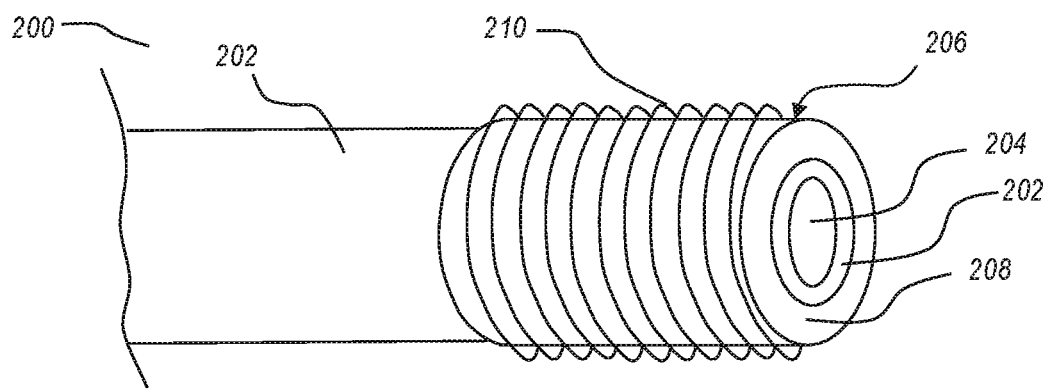
FIGS. 2A and 2B illustrate another embodiment of a hollow solenoid delivery device having a tapered catheter component.
Figure 2B:
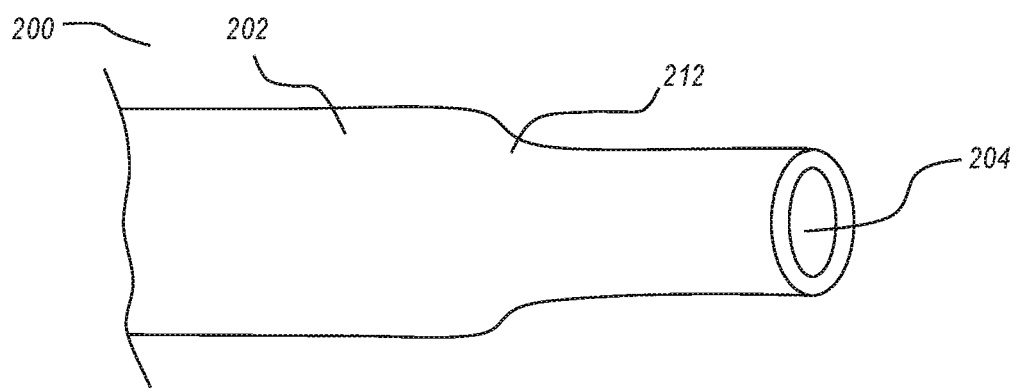

FIGS. 2A and 2B illustrate an alternative embodiment of an occlusion device 200 in which the catheter 202 is shaped so as to maintain a substantially flush outer diameter between the solenoid 206 and the more proximal sections of the catheter 202. FIG. 2A illustrates the occlusion device 200 including a solenoid 206 (having a core 208 and a coil 210) and a catheter 202 extending through the core 208 to a distal opening 24 (similar to the embodiment illustrated in FIG. 1A). As shown, the outer diameter of the solenoid 206 is substantially aligned with the outer diameter of the catheter 202 as the catheter 202 extends proximally from the solenoid 206. FIG. 2B illustrates the occlusion device 200 with the solenoid 206 removed so as to show a tapered section 212 of the catheter 202.

The tapered section 212 may be configured in size and shape to provide a desired relationship between the catheter 202 and the solenoid 206. In the illustrated embodiment, the tapered section 212 is configured to provide a substantially continuous outer diameter between the solenoid 206 and the proximally extending section of the catheter 202. In other embodiments, the catheter 202 may include a differently configured tapered section 212 and/or other structural components to provide a different positional relationship between the solenoid 206 and the catheter 202. For example, the difference in outer diameter between the catheter 202 and solenoid 206 may be set according to the structure of the tapered section 212. In some embodiments, for example, the outer diameter of the solenoid 206 may be smaller than the outer diameter of other more proximal sections of the catheter 202.

FIGS. 3A-3D illustrate cross-sectional views of various embodiments of occlusion devices. In FIGS. 3A-3D, the cross-sections are taken at distal sections of the devices where both catheter and solenoid components are engaged with one another. FIGS. 3A-3D may include one or more components described in relation to FIGS. 1A to 2B, as well as other embodiments described herein, and the corresponding description may therefore be applied to the embodiments of FIGS. 3A-3D as applicable.

Figure 3A:
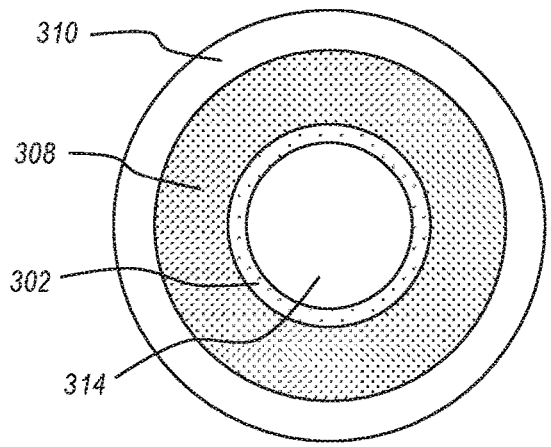
FIGS. 3A to 3D illustrate cross-sectional views of various embodiments of hollow solenoid delivery devices.
Figure 3B:
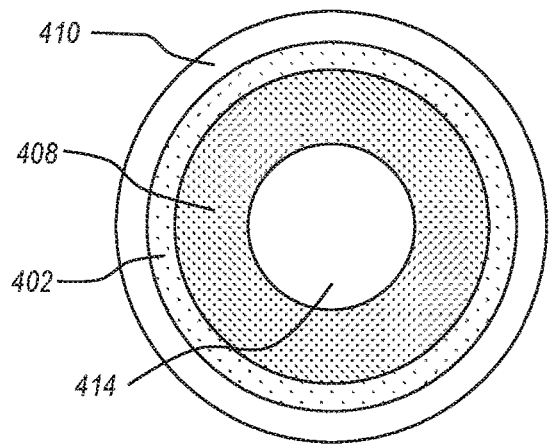
Figure 3C:
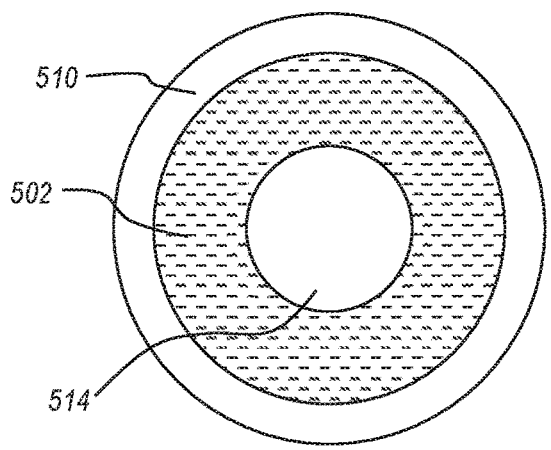
Figure 3D:
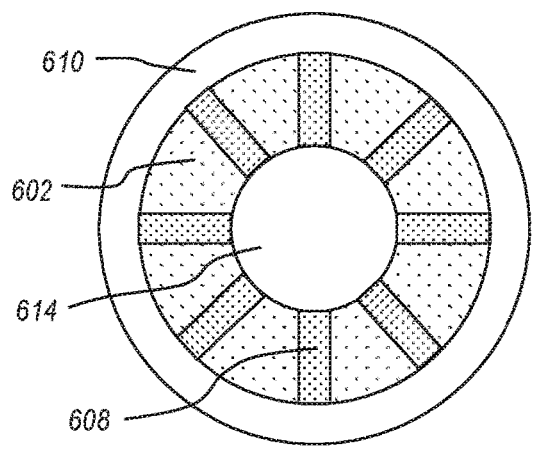

FIG. 3A illustrates an embodiment in which a catheter 302 defines a central lumen 314. The catheter 302 is encompassed by a solenoid core 308. The solenoid core 308 is encompassed by a solenoid coil 310. FIG. 3B illustrates an embodiment in which a solenoid core 408 defines a central lumen 414. The solenoid core 408 is encompassed by a catheter 402. The catheter 402 is encompassed by a solenoid coil 410. FIG. 3C illustrates an embodiment in which a catheter 502 defines a central lumen 514. In this embodiment, at least a portion of the catheter 502 includes an amount of embedded ferrous particles (e.g., iron and/or other materials having high magnetic permeability as described herein) so as to enhance the magnetic permeability of the catheter. The catheter 502 is encompassed by a solenoid coil 510. FIG. 3D illustrates an embodiment in which a catheter 602 defines a central lumen 614. In this embodiment, the catheter 602 includes a number of strips 608 of ferrous material (e.g., iron and/or other materials having high magnetic permeability as described herein) so as to enhance the magnetic permeability of the catheter 602. The catheter 602 is encompassed by a solenoid coil 610.

The embodiments shown in FIGS. 3A-3D are beneficially arranged to provide solenoids having a hollow configuration. Such embodiments are capable of providing selective electromagnetic functionality while also providing a central lumen through which a ferrofluid may be effectively routed. Advantageously, one or more embodiments described herein are capable of effectively delivering a ferrofluid to a targeted area while also directing a generated magnetic field toward the same targeted area. One or more of the described embodiments are thereby able to align the generated magnetic field with the delivery path of the ferrofluid, enabling effective control over the position of the delivered ferrofluid. In contrast, an occlusion device in which a solenoid or other magnetic field generator is offset from or otherwise not aligned with a delivery catheter will generate a magnetic field not in axial alignment with the delivery path of any delivered ferrofluid or other delivered material. Such an offset/misaligned configuration can reduce the ability to effectively manipulate an amount of delivered ferrofluid.

Figure 4:
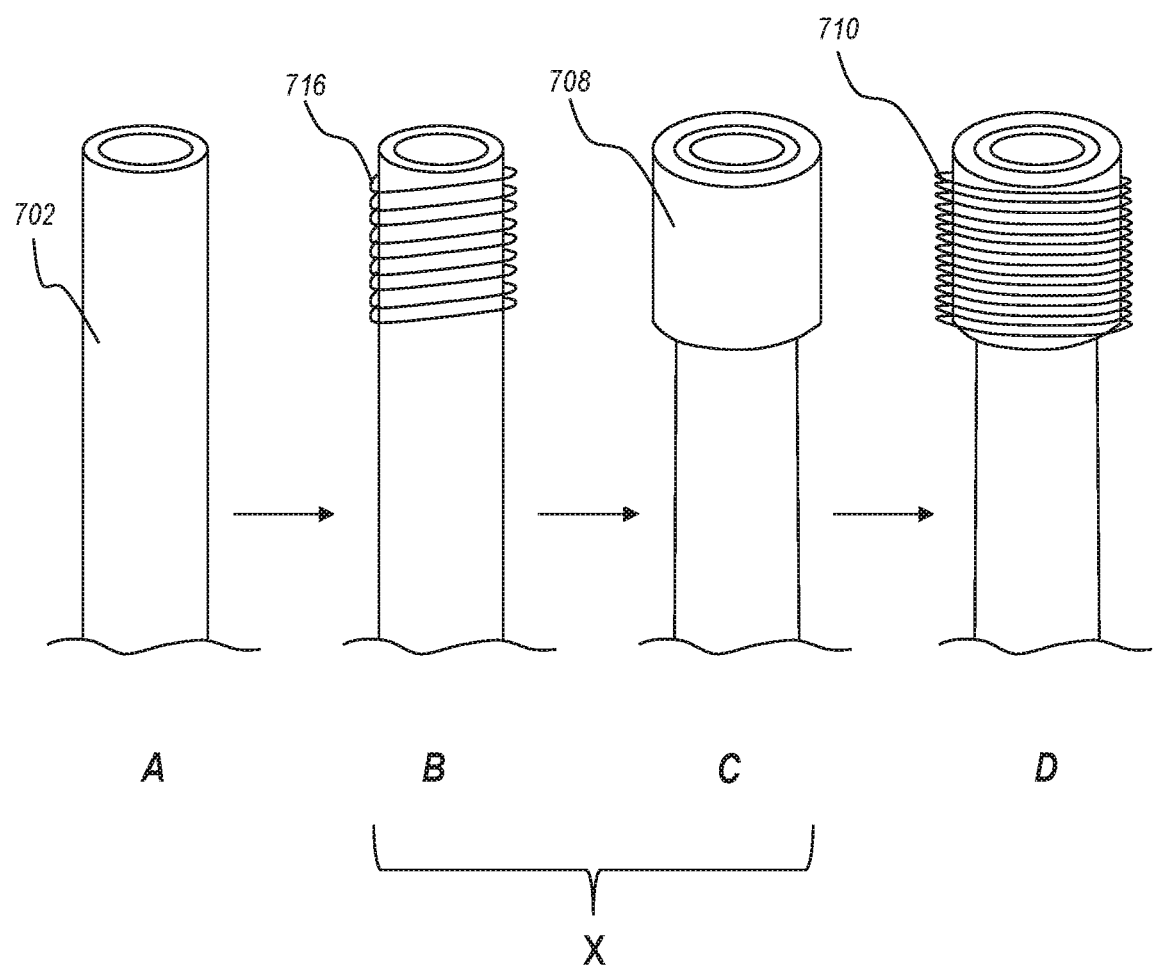
FIG. 4 illustrates an exemplary manufacturing process for manufacturing a hollow solenoid delivery device.

FIG. 4 illustrates an embodiment of a manufacturing process for forming an occlusion device, such as one or more of the occlusion device embodiments described herein. As shown in step "A," a catheter 702 having at least one lumen is provided. The catheter 702 may have a substantially uniform cross-section, as shown, or may have a discontinuous cross-section (e.g., tapered as in FIGS. 2A and 2B or otherwise tapered). The catheter 702 may have a circular cross-section, as shown, or may have a cross-section including one or more portions having cross-sectional shapes that are ovoid, polygonal, erratic, or otherwise shaped. The catheter 702 is configured for effective delivery of a ferrofluid through the at least one lumen. In preferred embodiments, the catheter 702 is configured for effective delivery of a ferroadhesive, such as a cyanoacrylate tissue glue having a concentration of ferrous nanoparticles effective to impart magnetic responsiveness to the tissue glue.

In step "B," a distal section of the catheter 702 is wrapped in a wire 716 formed from a magnetically permeable material. In presently preferred embodiments, the wire 716 comprises iron. In other embodiments, a wire formed from one or more additional or alternative materials having high magnetic permeability may be utilized. The wire 716 may be packed tightly around the distal section of the catheter 702 so as to form a base for the solenoid core of the device. The wire may be configured in size so as to provide a solenoid having desired electromagnetic properties (e.g., desired for a particular application or set of applications). In some embodiments, the wire 716 has a diameter measuring about 0.08 mm, 0.1 mm, 0.14 mm, 0.18 mm, 0.25 mm, 0.4 mm, 0.7 mm, 1 mm, or measuring within a range defined by any two of the foregoing values. For example, beneficial results have been shown using an iron wire material having a diameter of about 0.35 mm.

In step "C," a coating/paint is applied to the wire 716 to fill in interstitial spaces between adjacent turns of the wire 716 so as to form a core 708. The coating is preferably formed from a material having a high magnetic permeability, such as one or more of the materials described with respect to the wire 716. As indicated by the numeral "X," steps B and C may be repeated a number of times to provide a core having desired size, weight, and/or magnetic properties. For example, after a first layer of coating has been applied to form the solenoid core 708, another wire can be wrapped around the core (step B repeated) followed by the application of another layer of coating material (step C repeated).

In some embodiments, the core 708 is configured with 1 to 10 layers, or with 2 to 6 layers. In some embodiments, the core 708 is configured to have a weight within a range of about 0.3 g to 5 g, or about 0.6 g to 3.5 g. For example, iron cores formed within the foregoing weight range have been found to provide beneficial results. In embodiments having cores formed from different materials, the relative weight of the core may be adjusted from the foregoing weight ranges according to proportional differences in density between iron and the different materials. In step "D," a coil 710 is applied (e.g., wrapped around) the outside of the core 710 to complete the solenoid of the occlusion device.

Although the process shown by FIG. 4 illustrates one exemplary method for manufacturing an occlusion device, it will be understood that other processes may also be utilized to produce one or more of the disclosed occlusion devices.

For example, although FIG. 4 illustrates the manufacture of a solenoid core 708 using a combination of wire 716 and a coating/paint, other method and/or device embodiments may omit the use of a wire, such as by including pre-formed cores attached (e.g., adhered and/or mechanically fastened) to a catheter.

Figure 5A:
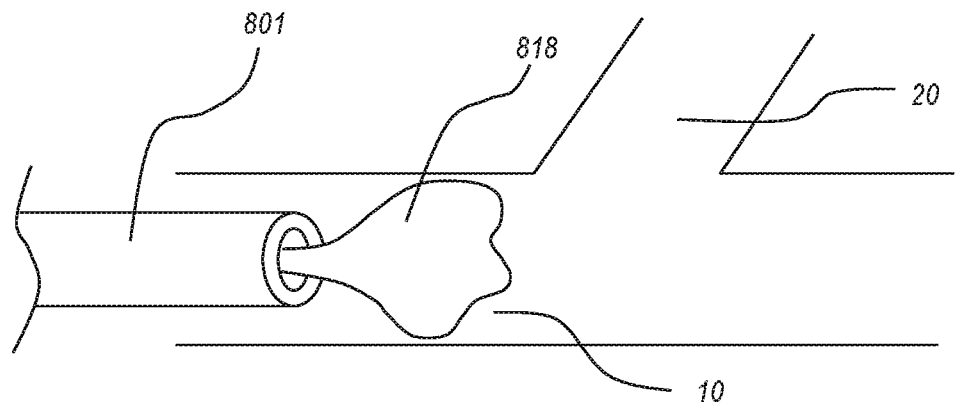
FIGS. 5A and 5B illustrate delivery of a ferrofluid to a targeted treatment site using a delivery catheter not configured to provide a magnetic field for controlling position of the ferrofluid.
Figure 5B:
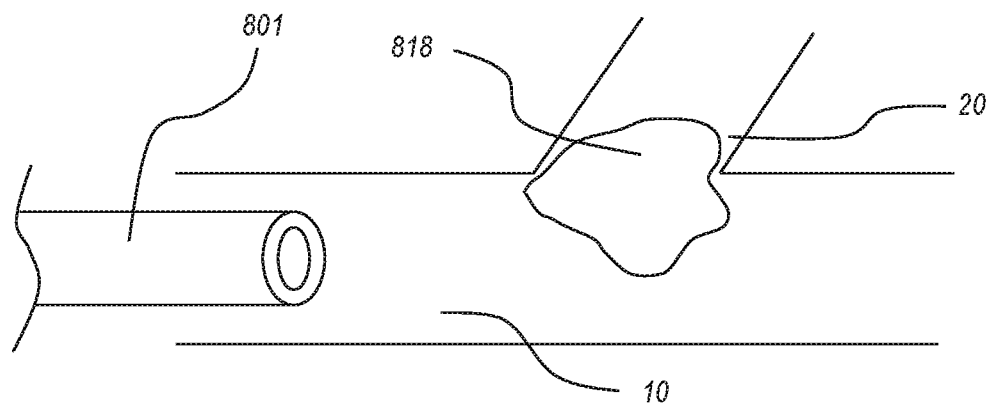

FIGS. 5A and 5B illustrate use of a catheter device 801 to deliver a ferrofluid to a targeted treatment site 10. The illustrated catheter device 801 is not configured with a hollow solenoid and associated electromagnet functionality. As shown in FIG. 5A, a bolus of ferrofluid 818 is delivered through the catheter device 801 near the targeted treatment site 10. However, as shown in FIG. 5B, because the catheter device 801 is unable to control the position of the bolus of ferrofluid 818, the bolus of ferrofluid 818 may undesirably migrate to non-targeted anatomical site 20. For example, the non-targeted anatomical site 20 could be an adjacent duct or vasculature structure which is otherwise healthy. In applications in which the ferrofluid 818 is a ferroadhesive, such a migration can lead to complications related to the formation of unwanted tissue plugs, while also failing to resolve the originally targeted pathology.

Figure 6A:
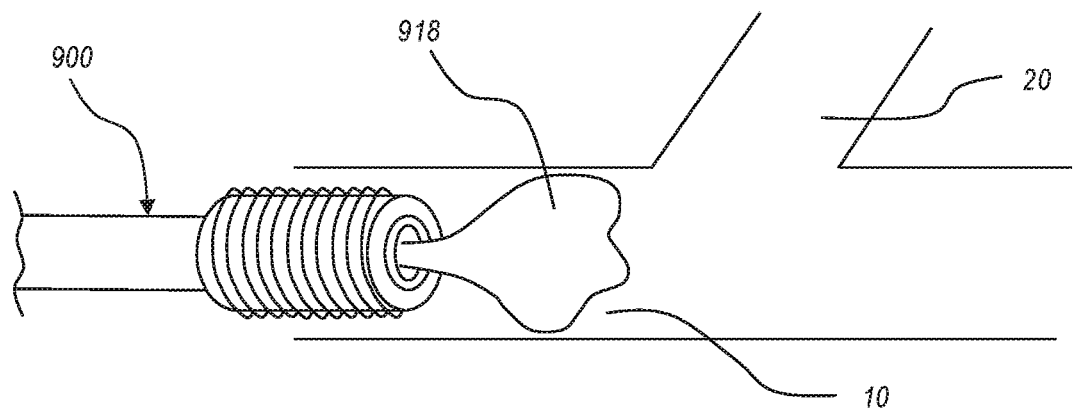
FIGS. 6A and 6B illustrate delivery of a ferrofluid to a targeted treatment site using a delivery device configured to provide a magnetic field for controlling position of the delivered ferrofluid.
Figure 6B:
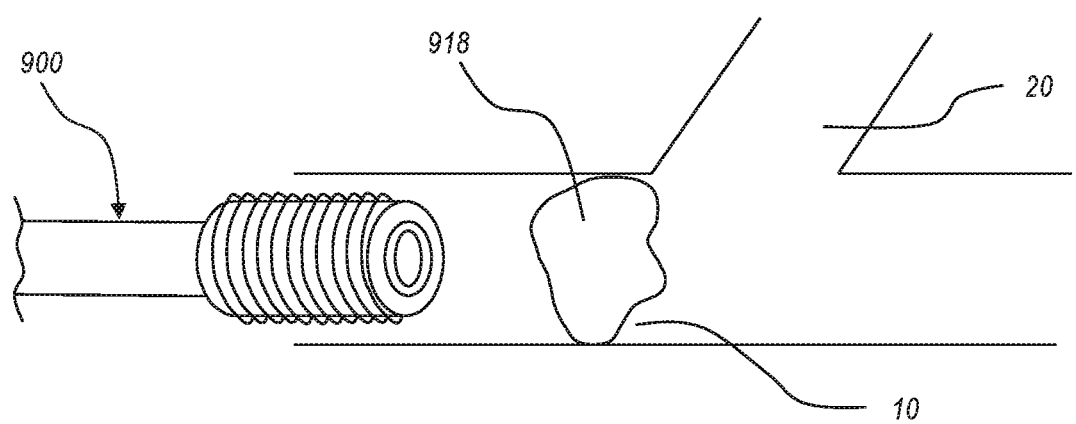

FIGS. 6A and 6B illustrate use of an occlusion device 900 to deliver a ferrofluid to the targeted treatment site 10. The occlusion device 900 may be configured as one of the other occlusion device embodiments described herein, or as a combination of different occlusion device components as described herein. As shown in FIG. 6A, a bolus of ferrofluid 918 is delivered to the targeted treatment site 10. As shown in FIG. 6B, after the ferrofluid 918 has been delivered, the magnetic functionality of the occlusion device 900 is able to maintain the position of the bolus of ferrofluid 918 at the targeted treatment site 10, preventing it from migrating to non-targeted anatomical site 20. For example, in an application in which the ferrofluid 918 is a ferroadhesive, the occlusion device 900 enables the formation of a properly positioned tissue plug at targeted treatment site 10, without damaging or undesirably occluding non-targeted anatomical site 20.

In some embodiments, the occlusion device 900 is configured so as to be able to maintain and/or control the position of a bolus of ferrofluid 918 having a weight of up to about 0.5 g, or up to about 0.75 g, or up to about 1 g, or up to about 2 g. In some embodiments, such activity may be accomplished using an applied current of about 5 amps or less, about 4 amps or less, about 3 amps or less, or about 2.5 amps or less.

In some embodiments, adjustment of one or more components can increase the strength and/or effectiveness of the generated magnetic field, and in some embodiments, the occlusion device 900 may be capable of controlling the position of a bolus of ferrofluid 918 weighing more than 2 g. For example, adjustments to the core (e.g., composition, weight, thickness) and/or adjustments to the coil (e.g., turns per unit axial length, wire composition) can increase the strength of a generated magnetic field. Additionally, or alternatively, increasing applied current can increase the strength of the generated magnetic field. Additionally, or alternatively, adjusting the composition of the associated ferrofluid (e.g., by increasing the concentration of included ferrous particles) can increase the responsiveness of the ferrofluid to the generated magnetic field.

Figure 7A:
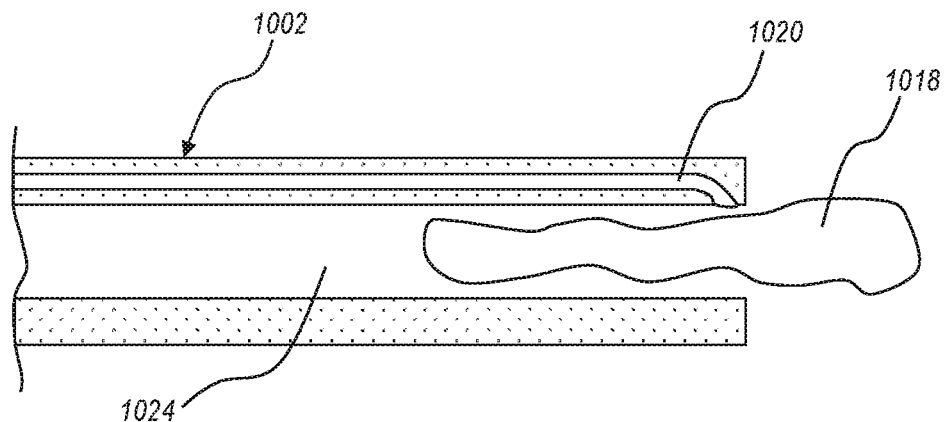
FIGS. 7A and 7B illustrate an embodiment of a catheter having a lumen configured for providing a separating force for separating the catheter from a bolus of delivered ferrofluid.
Figure 7B:
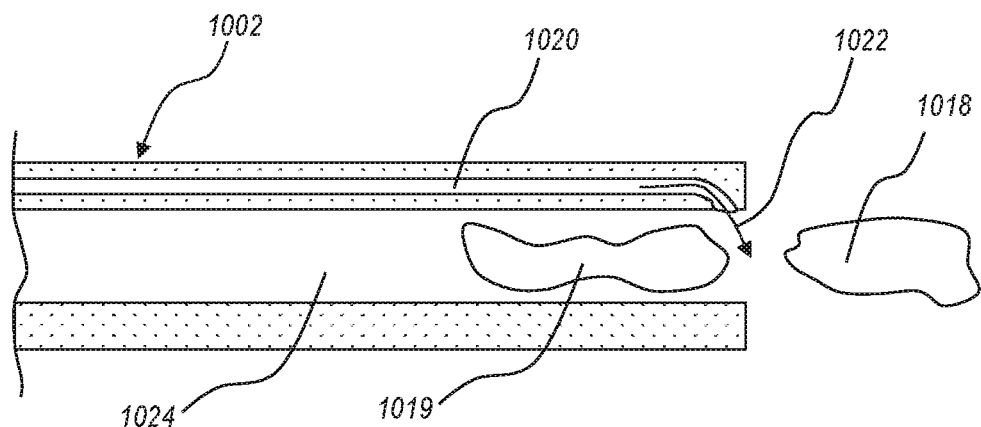

FIGS. 7A and 7B illustrate cross-sectional views of an embodiment of a catheter 1002 that may be utilized with one or more of the occlusion device embodiments described herein. As shown, the catheter 1002 includes a first lumen 1024 configured for delivery of a ferrofluid 1018. As shown in FIG. 7A, in some circumstances, a bolus of delivered ferrofluid 1018 may not completely exit the catheter 1002 when delivered to a targeted treatment site. For example, more ferrofluid may be routed through the catheter 1002 than is necessary to complete the desired treatment and/or an amount external to the catheter 1002 may remain associated with an amount still within the catheter 1002.

Particularly in instances in which the ferrofluid 1018 is a ferroadhesive, complications can result if the bolus of ferrofluid 1018 is not sufficiently separated from the catheter 1002. For example, the catheter 1002 may need to maintain proximity to the ferrofluid 1018 to control the position of the ferrofluid 1018 for a time sufficient to form an effective occlusion, but also needs to avoid getting stuck within the occlusion and needs to be removable from the treatment site without disrupting the newly formed occlusion.

The illustrated catheter 1002 also includes a second lumen 1020 configured to deliver a separating force to separate an external portion of the ferrofluid 1018 from a remaining portion still within the catheter 1002. As shown in FIG. 7B, a fluid (gas and/or liquid) is deliverable through the second lumen 1020, as indicated by arrow 1022, to separate the external portion of the ferrofluid 1018 from an internal remainder 1019. This separation allows the catheter 1002 to be separated from the ferrofluid 1018 while still maintaining proximity to provide control over the position of the ferrofluid 1018.

Figure 8A:
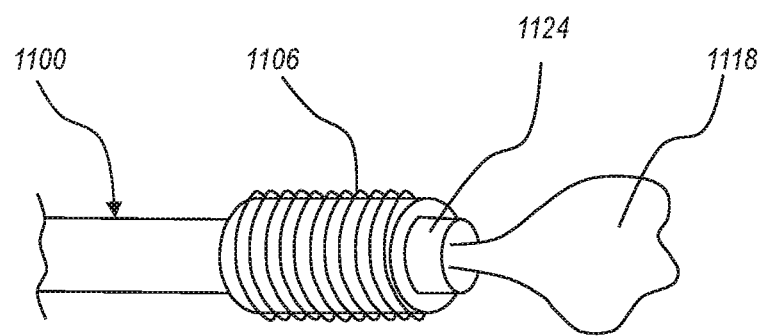
FIGS. 8A and 8B illustrate an embodiment of a delivery device having a breakaway distal section.
Figure 8B:
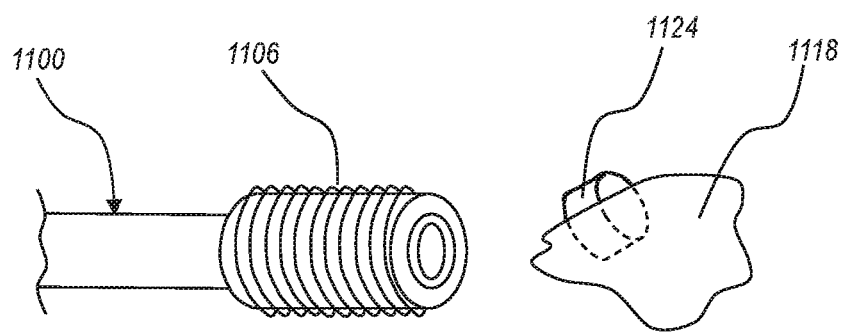

FIGS. 8A and 8B illustrate another embodiment of an occlusion device 1100. The illustrated embodiment is configured with a breakaway distal end 1124. As shown in FIG. 8A, as a ferrofluid 1118 is delivered from the occlusion device 1100, a portion of the ferrofluid 1118 may remain in contact with the device 1100 and/or may not completely separate from the device 1100. As described above, the device 1100 needs to be removable from the ferrofluid 1118 but also is preferably capable of being held in proximity to the ferrofluid 1118 to control the position of the ferrofluid 1118 (e.g., while it cures to form an occlusion). As illustrated in FIG. 8B, the breakaway distal end 1124 is detachable from the solenoid 1106 and other more proximal sections of the device 1100. The breakaway distal end 1124 can remain with the delivered bolus of ferrofluid 1118, allowing the remainder of the device 1100 to be freely repositioned and removed with respect to the ferrofluid 1118.

Figure 9:
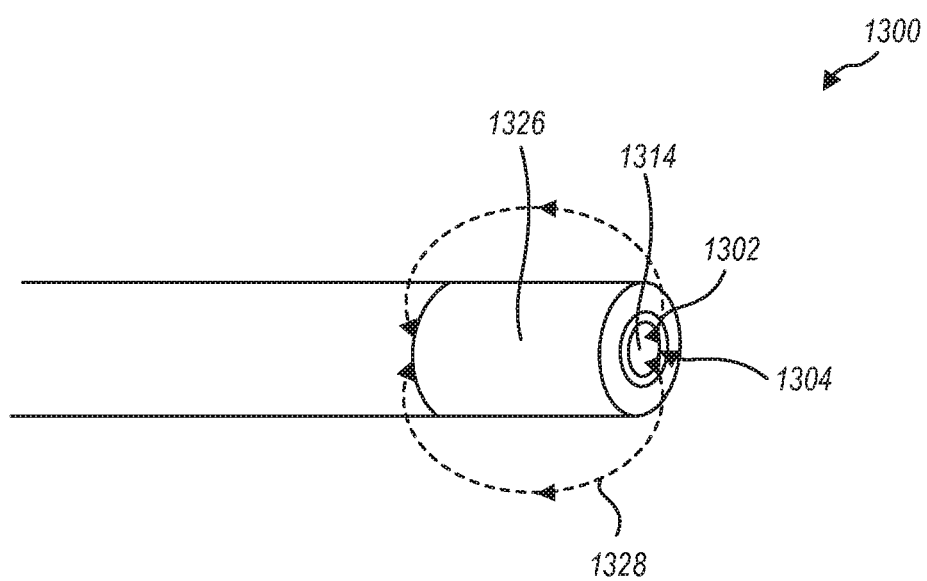
FIG. 9 is a representation of an occlusion device.

FIG. 9 is a representation of an occlusion device 1300, according to at least one embodiment of the present disclosure. In the embodiment shown, the occlusion device 1300 includes a magnet 1326. In some embodiments, the magnet 1326 may be any type of magnet. For example, the magnet 1326 may be a permanent magnet, such as ferrite, alnico, rare earth magnets (e.g., neodymium, samarium-cobalt), iron bar magnets, any other type of permanent magnet, and combinations thereof.

In some embodiments, the magnet 1326 may be any other type of magnet. For example, the magnet 1326 may be a solenoid, as discussed in further detail herein. In some embodiments, the magnet 1326 may be an electromagnet.

The occlusion device 1300 may include a catheter 1302 having a distal opening 1304. The magnet 1326 may extend around (e.g., encompass) at least a portion of the catheter 1302 at the distal opening 1304. In some embodiments, a ferrofluid may pass through a central lumen 1314 in the catheter to the distal opening 1304. Thus, the ferrofluid may pass through a hollow center of the magnet 1326 as it passes through the central lumen 1314 to the distal opening 1304.

The magnet 1326 may have a magnetic field 1328. In some embodiments, such as in embodiments including a permanent magnet 1326, the magnetic field 1328 may be permanent, or may be constantly applied. In this manner, when a ferrofluid passes through the occlusion device 1300, the ferrofluid may be held in place at or near the distal opening 1304.

In some embodiments, using a permanent magnet 1326 may simplify the occlusion device 1300. For example, a permanent magnet 1326 may prevent the need power a solenoid or other electromagnet. This may reduce the complexity of the catheter 1302, thereby decreasing manufacturing costs. Furthermore, a permanent magnet 1326 may simplify application of the ferrofluid by reducing the number of steps for implementation. This may allow a health care provider to focus on placement of a bolus of ferrofluid, rather than on curing and/or solidifying the ferrofluid.

Figures 3, 10:
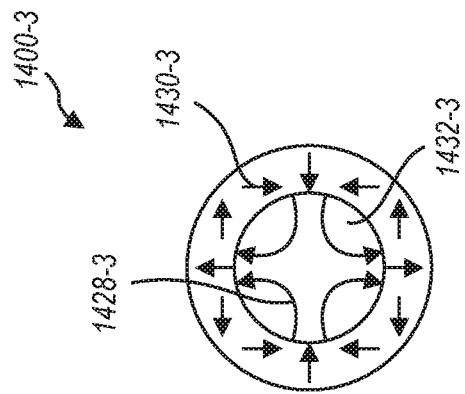
FIGS. 10-1 through FIG. 10-3 are representations of cross-sectional views of a magnet coupled to a catheter.
Figures 2, 10:
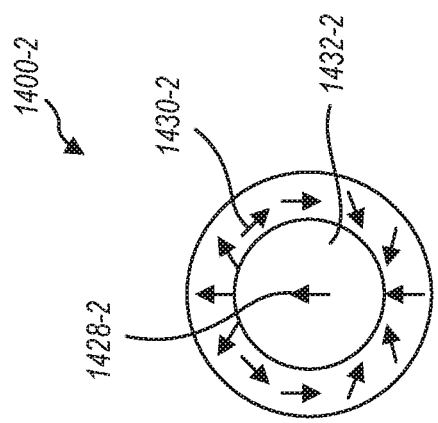
Figures 1, 10:
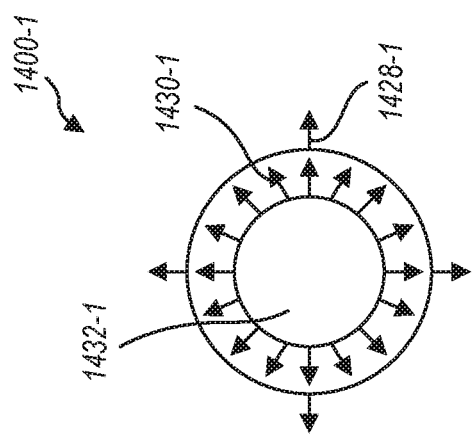

FIG. 10-1 through FIG. 10-3 are representations of magnets (collectively 1400), according to embodiments of the present disclosure. The magnets 1400 may have a polarity arrangement (collectively 1430). The polarity arrangement may be the arrangement of the polarity of magnetic fields in the magnets 1400. The polarity arrangement may at least partially determine the strength and direction of the magnetic field (collectively 1428).

In accordance with embodiments of the present disclosure, the magnets 1400 may be arranged with any polarity arrangement 1430. For example, the magnets 1400 may be arranged in a Halbach array, such as a Halbach cylinder. A Halbach array is an arrangement of magnetic polarities that aligns the magnetic fields 1428 to be stronger in some locations and weaker in other locations. For example, on a linear Halbach array, a magnetic field may be small or negligible on one side of the array, and stronger (e.g., double or close to double) strength on the other side of the array, compared with a continuous magnet of similar size.

In FIG. 10-1, the magnet 1400-1 is arranged with a polarity arrangement 1430-1 in a Halbach cylinder. The polarity arrangement 1430-1 is such that there no, a negligible, or a small magnetic field 1428-1 in the center 1432-1 of the magnet 1400-1. In this manner, as a ferrofluid is passed through the center 1432-1 of the magnet 1400-1, the magnetic elements of the ferrofluid may not react with the magnetic field 1428-1 until the ferrofluid exits the magnet 1400-1 (e.g., through the distal opening 1304 of FIG. 10). This may help prevent the center 1432-1 of the magnet 1400-1 from becoming clogged with the ferrofluid. This may further help prevent the ferrofluid from setting in the center 1432-1 of the magnet 1400-1. In this manner, placement accuracy of the size and placement of the bolus of ferrofluid may be improved.

In FIG. 10-2, the magnet is arranged in a Halbach cylinder with a polarity arrangement 1430-2 in a Halbach cylinder. The polarity arrangement 1430-2 is such that the magnetic field 1428-2 in the center 1432-2 of the magnet 1430-2 is unidirectional. This may allow for control of the location of the bolus of ferrofluid in the center 1432-2 of the magnet 1430-2. For example, the polarity arrangement 1430-2 may allow the ferrofluid to be directed to one side of the magnet 1430-2, thereby allowing for additional fluid to pass through the center 1432-2 of the magnet. This may further increase control of the location of the bolus of ferrofluid. For example, if a target location is a fistula located on one side of a blood vessel, the polarity arrangement 1432-2 may help to direct the bolus of ferrofluid into the fistula. This may reduce the amount of ferrofluid needed to fill the fistula.

In FIG. 10-3, the magnet 1400-3 is arranged in a Halbach cylinder with a polarity arrangement 1430-3. The polarity arrangement 1430-3 is such that the magnetic field 1430-3 in the center 1432-3 is multi-directional. This may allow for additional control over the placement of ferrofluid within the center 1432-3 of the magnet 1400-3. For example, the polarity arrangement 1430-3 may centralize the ferrofluid within the center 1432-3 of the magnet 1400. In this manner, the bolus of ferrofluid may be formed within the center 1432-3 of the magnet 1400-3, and then ejected from the center 1432-3 of the magnet 1400-3 when the bolus is formed into the desired size and shape.

While the embodiments of FIG. 10-1 through FIG. 10-3 have been described with specific polarity arrangements 1430, it should be understood that other polarity arrangements 1430 may be used. Embodiments of the present disclosure may include any polarity arrangement of a magnet 1400 and may be used to control placement of the bolus of ferrofluid.

Figure 11:
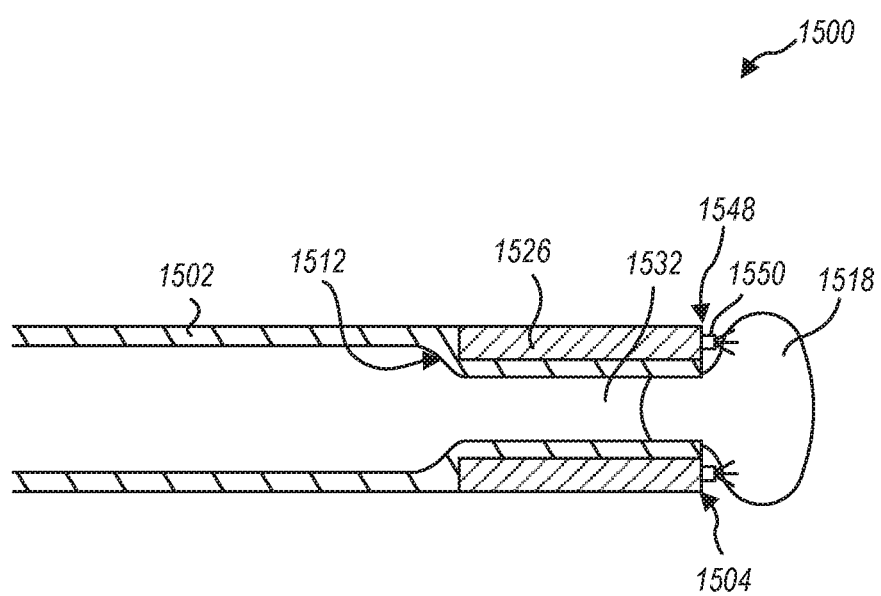
FIG. 11 is a representation of a cross-sectional view of an occlusion device.

FIG. 11 is a representation of a cross-sectional view of an occlusion device 1500, according to at least one embodiment of the present disclosure. The occlusion device 1500 includes a catheter 1502 having a lumen extending therethrough to a distal opening 1504 at a distal end of the catheter. The catheter 1502 includes a tapered portion 1512 where a diameter of the catheter 1502 is reduced. In the embodiment shown, a magnet 1526 is coupled to the catheter 1502 such that the magnet 1526 encompasses the portion of the catheter 1502 distal the tapered portion 1512.

The magnet 1526 is coupled to the catheter 1502 so that the catheter is configured to deliver a ferrofluid 1518 past the magnet 1526 (e.g., past the distal end 1504 of the occlusion device 1500). In this manner, the ferrofluid 1518 may be delivered to a target treatment site. To allow ferrofluid 1518 past the magnet 1526, the magnet includes a bore through the center 1532 of the magnet. The bore may encompass the portion of the catheter 1502 that extends through the center 1532 of the magnet 1526.

In the embodiment shown, the ferrofluid 1518 has been pushed at least partly out of the distal end 1504 of the catheter 1502, forming a bolus. The bolus of ferrofluid 1518 may be, at least partially, held in place by a magnetic force from the magnet 1526. In some embodiments, the ferrofluid 1518 may be any type of ferrofluid.

In some embodiments, the ferrofluid 1518 may include an adhesive. In some embodiments, the ferrofluid 1518 may include a ferroadhesive. In other words, the ferrofluid 1518 may include an adhesive that solidifies when a magnetic field is applied to it. In some embodiments, the ferroadhesive may have a set time, or an amount of time before the ferroadhesive becomes solid after the application of the magnetic field. For example, the magnet 1526 may apply the magnetic field to the ferroadhesive after the ferrofluid 1518 passes through the center 1532 of the magnet 1526.

In some embodiments, the ferrofluid 1518 may include a non-magnetically activated adhesive. For example, the ferrofluid 1518 may include an adhesive that has a set time (e.g., an amount of time before the ferrofluid 1518 becomes solid). The ferrofluid 1518 may include magnetic properties such that the magnet 1526 may control a position of the ferrofluid. For example, and as discussed herein, the magnet 1526 may be of sufficient strength to hold the bolus of ferrofluid 1518 at the target treatment site. In some embodiments, the magnet 1526 may be of sufficient strength to direct the bolus of ferrofluid 1518 to the target treatment site. The magnet 1526 may then hold the bolus of ferrofluid 1518 at the target treatment site until the adhesive in the ferrofluid has set.

In some embodiments, the distal end 1548 of the catheter 1502 may include an auxiliary curing device 1550. The auxiliary curing device 1550 may help to cure the bolus of ferrofluid 1518. For instance, as discussed herein, the ferrofluid 1518 may set based on the application of a magnetic field, based on a time since mixing, or based on any other mechanism. The ferrofluid 1518 may set over a period of time. This may allow the medical professional time to place the ferrofluid 1518 into the desired location. Once the ferrofluid 1518 is in location, the auxiliary curing device 1550 may speed up the curing process. In this manner, the healthcare professional may manipulate the ferrofluid 1518 into a desired shape and/or location. Once the ferrofluid 1518 is in place, to prevent the ferrofluid 1518 from moving while curing, the auxiliary curing device 1550 may speed up the curing process.

In some embodiments, the auxiliary curing device 1550 may increase the curing time of the ferrofluid 1518 using any mechanism. For example, the auxiliary curing device 1550 may include an ultraviolet (UV) light source. The ferrofluid 1518 may be sensitive to UV light and set when the UV light is applied. In some embodiments, the auxiliary curing device 1550 may include any other mechanism, including radio frequency waves, sound waves, and so forth.

Figure 12:
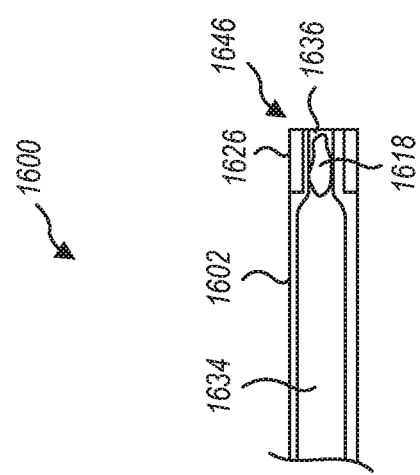
FIG. 12 is a representation of a partial cut-away view of an occlusion device.
Figure 12:
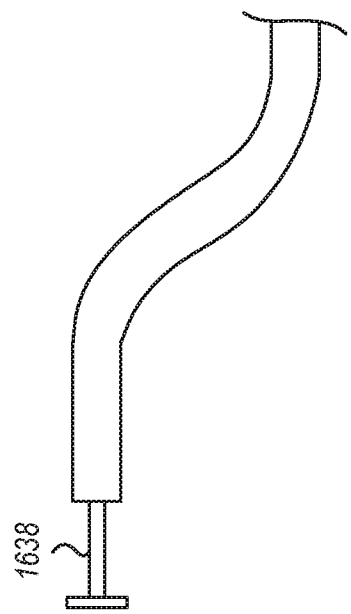

FIG. 12 is a representation of a cut-away view of an occlusion device 1600, according to at least one embodiment of the present disclosure. The occlusion device 1600 includes a catheter 1602 having a lumen 1634 extending therethrough. A magnet 1626 may be coupled to the catheter 1602 at a distal end of the catheter 1602.

In the embodiment shown, a bolus of ferrofluid 1618 is located in a bore 1636 of the magnet 1626. In some embodiments, the bolus of ferrofluid 1618 may set while in the bore 1636. In some embodiments, the adhesive within the ferrofluid 1618 may adhere to the walls of the bore 1636.

To remove the bolus of ferrofluid 1618, the occlusion device 1600 includes an ejection mechanism 1638. The ejection mechanism 1638 may provide additional force to the bolus of ferrofluid 1618 in the catheter 1602 and/or the bore 1636. The additional force may break the contact between the bolus of ferrofluid 1618 and the walls of the bore 1636. In some embodiments, the bolus of ferrofluid may be partially inside and partially outside of the bore 1636. When the bolus of ferrofluid 1618 is set, the ejection mechanism 1638 may cause the bolus of ferrofluid 1618 to disconnect from the occlusion device. In this manner, a health care provider may develop a bolus of ferrofluid that has any desired size and shape characteristics.

The ejection mechanism 1638 may be any mechanism which allows additional force to be applied to the bolus of ferrofluid 1618 in the bore 1636. For example, the ejection mechanism 1638 may be a plunger at a proximal end of the occlusion device 1600. When the plunger is plunged, the plunger may increase the fluid pressure inside the catheter 1602. The fluid pressure may apply a force to the bolus of ferrofluid 618. The force may then overcome the adhesive force of where the bolus of ferrofluid has adhered to the walls of the bore 1636.

In some embodiments, the ejection mechanism 1638 may be located at a distal end of the catheter 1602. For example, the ejection mechanism 1638 may be a detachable portion of the catheter 1602 and/or the magnet 1626. For example, the ejection mechanism 1638 may be a detachable portion as described in reference to FIG. 8A and FIG. 8B. In some examples, the ejection mechanism may include a second lumen that is configured to deliver a separating force, such as described in reference to FIG. 7A and FIG. 7B. In some embodiments, the ejection mechanism 1638 may be any ejection mechanism configured to eject or separate the bolus of ferrofluid 1618 from the catheter 1602.

In some embodiments, the distal end 1648 of the catheter 1602, or a portion of the distal end 1648 of the catheter 1602, may be coated with an anti-stick coating. For example, the distal end 1648 may be coated with a polymer to which the ferrofluid 1618 does not easily bond. In this manner, the bolus 1626 of ferrofluid may easily release from the distal end 1648 of the catheter 1602 after the ferrofluid has set. In some embodiments, the anti-stick coating may be any type of polymer, such as a silicone based polymer. In some embodiments, the anti-stick coating on the distal end 1648 of the catheter may be utilized in addition to any ejection mechanisms 1638, separating forces, separating tips, or other mechanism to separate the bolus 1626 of ferrofluid from the distal end 1648 from the catheter.

Figure 13:
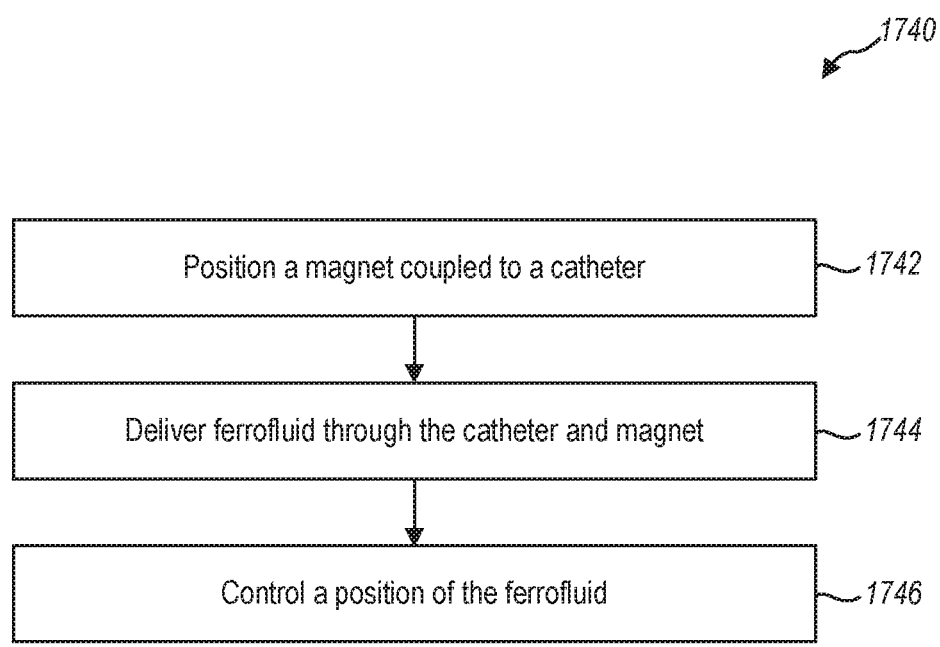
FIG. 13 is a representation of a method of delivering a ferrofluid to a targeted treatment site.

FIG. 13 is a representation of a method 1740 of delivering a ferrofluid to a targeted treatment site, according to at least one embodiment of the present disclosure. The method 1740 may include positioning a magnet coupled to a distal end of a catheter near the targeted treatment site at 1742. In some embodiments, positioning the catheter may include inserting the catheter into a blood vessel of a patient and extending the catheter through the blood vessel to the targeted treatment site.

The method 1740 may further include delivering an amount of the ferrofluid through the catheter and the magnet to the targeted treatment site at 1744. In some embodiments, the ferrofluid may pass through both the catheter and the magnet simultaneously. For example, the catheter and the magnet may be concentric, and the magnet may at least partially encompass a portion of the catheter. The ferrofluid may pass through the section of the catheter that is encompassed by the ferrofluid, such that the ferrofluid passes through both the catheter and the magnet simultaneously, at the same time, or at the same longitudinal position of the catheter.

The method 1740 may further include controlling a position of the ferrofluid using a magnetic field generated by the magnet at 1746. In some embodiments, controlling the position of the ferrofluid may include preventing the ferrofluid from exiting the catheter. In some embodiments, controlling the position of the ferrofluid includes maintaining the position of the ferrofluid until an adhesive in the ferrofluid has set. In some embodiments, controlling the position of the ferrofluid includes constantly applying the magnetic field generated by the magnet, such as a constant magnetic field applied by a permanent magnet. In some embodiments, the method 1740 may include generating a permanent magnetic field using a permanent magnet. In some embodiments, the method 1740 may include placing a bolus of the ferrofluid using the distal end of the catheter and the magnetic field generated by the magnet.

In some embodiments, the method 1740 may include ejecting the ferrofluid from the catheter using an ejection mechanism. For example, ejecting the ferrofluid may include depressing a plunger, causing a fluid pressure in the catheter to increase. The increased fluid pressure may cause the bolus of ferrofluid to release from the catheter.

EXAMPLES

Delivery devices were manufactured according to the process illustrated in FIG. 4. The catheters were 5 Fr Bernstein catheters. The cores were formed using alternating layers of iron wire (0.33 mm) and iron paint (49.97% wt.

iron). The solenoids had axial lengths of about 2 cm at the distal ends of respective catheters.

Three prototypes of separate experimental groups were built according to the specifications shown in Table 1. Group 2 indicates two alternating coats of iron wire and iron paint were used for the core. Group 3 indicates four alternating coats of iron wire and iron paint were used for the core. Group 4 indicates six alternating coats of iron wire and iron paint were used for the core. A, B, or C indicates the version number of that group. Three versions of each experimental group were built in order to analyze differences between and among prototypes. Weights were taken during the manufacturing process to determine similarity between prototypes of the same number and differences between different group numbers.

TABLE 1

| | Relative Weight (g) | | | | | | | | |
|---|---|---|---|---|---|---|---|---|---|
| Prototype | 2A | 2B | 2C | 3A | 3B | 3C | 4A | 4B | 4C |
| Catheter weight | 0.33 | 0.35 | 0.37 | 0.28 | 0.36 | 0.35 | 0.34 | 0.35 | 0.45 |
| 1 wire | 0.25 | 0.24 | 0.25 | 0.30 | 0.26 | 0.22 | 0.22 | 0.23 | 0.23 |
| 1 paint | 0.02 | 0.02 | 0.02 | 0.02 | 0.03 | 0.04 | 0.04 | 0.02 | 0.03 |
| 2 wire | 0.30 | 0.29 | 0.30 | 0.31 | 0.29 | 0.31 | 0.30 | 0.29 | 0.31 |
| 2 paint | 0.08 | 0.09 | 0.06 | 0.09 | 0.01 | 0.08 | 0.08 | 0.05 | 0.06 |
| 3 wire | | | | 0.30 | 0.38 | 0.35 | 0.39 | 0.35 | 0.37 |
| 3 paint | | | | 0.13 | 0.10 | 0.17 | 0.13 | 0.05 | 0.11 |
| 4 wire | | | | 0.43 | 0.42 | 0.09 | 0.46 | 0.40 | 0.47 |
| 4 paint | | | | 0.18 | 0.17 | 0.54 | 0.27 | 0.18 | 0.21 |
| 5 wire | | | | | | | 0.63 | 0.48 | 0.59 |
| 5 paint | | | | | | | 0.41 | 0.36 | 0.38 |
| 6 wire | | | | | | | 0.76 | 0.77 | 0.90 |
| 6 paint | | | | | | | 0.37 | 0.72 | 0.40 |
| Iron Core Weight | 0.60 | 0.59 | 0.59 | 1.55 | 1.51 | 1.39 | 3.40 | 3.20 | 3.46 |
| Avg | | 0.59 | | | 1.48 | | | 3.35 | |
| Stdev | | 0.00 | | | 0.08 | | | 0.14 | |

Coat number and material in the left column indicate the step in the manufacturing process depicted in FIG. 6 at which the weight was taken. For instance: 3 paint means the weight of the prototype after alternating 3 coats of wire and 3 coats of paint were applied to the core.

After drying, an external coil was constructed using coated copper wire with a diameter of 0.33 mm wrapped tightly approximately 35 times around the iron core. This coil was connected to the power supply in order to create the magnetic field.

Three sets of experiments were conducted to verify the presence of a magnetic field. In the first setup, each prototype was set in a slim track and secured. A 3 mm steel ball was placed 3 mm away from the distal end of the solenoid and the power supply was turned on. The current through the external coil was increased until the magnetic field pulled the steel ball towards the solenoid. The voltage, current, and power were recorded at this instant. The power was turned off and the ball was returned to the start position. Every third trial the entire setup was redone to address potential setup bias. Nine trials were performed for each of the six prototypes in experimental groups 2 and 3. Group 4 was excluded from this experiment because its large size did not fit in the track. It also was much larger than the diameter of the steel ball used.

Each prototype moved the ball within the limits of the power supply, no more than 3 A of current. Results indicate that solenoids on this scale can be used to move magnetically reactive materials. Tables 2 to 4 show the results for each of the prototypes evaluated in the horizontal experimental setup.

TABLE 2

| | Current | |
|---|---|---|
| Prototype | Mean (A) | Std. Dev. |
| 2A | 2.62 | 0.25 |
| 2B | 2.05 | 0.13 |
| 2C | 2.37 | 0.25 |
| 3A | 2.29 | 0.41 |
| 3B | 2.58 | 0.25 |
| 3C | 2.73 | 0.16 |

TABLE 3

| | Voltage | |
|---|---|---|
| Prototype | Mean (A) | Std. Dev. |
| 2A | 1.46 | 0.15 |
| 2B | 1.08 | 0.09 |
| 2C | 1.28 | 0.13 |
| 3A | 1.30 | 0.29 |
| 3B | 1.69 | 0.14 |
| 3C | 1.75 | 0.07 |

TABLE 4

| | Power | |
|---|---|---|
| Prototype | Mean (W) | Std. Dev. |
| 2A | 3.89 | 0.76 |
| 2B | 2.21 | 0.31 |
| 2C | 3.04 | 0.63 |
| 3A | 3.07 | 1.26 |
| 3B | 4.39 | 0.75 |
| 3C | 4.79 | 0.48 |

In a second experimental setup, prototype was secured vertically and connected to the power supply. The power was turned to a maximum level of approximately 3 A, and the 3 mm steel ball was allowed to hang off the distal end of the prototype. The power was turned down incrementally until the ball fell off. This experiment was used to determine feasibility of using a clinically applicable total weight. A third setup used two 3 mm steel balls weighing a combined total of 0.7427 g. It was determined through discussion with physicians who would potentially use this device that it needed to be able to lift 0.52 g. The experimental set up accounted for a 50% increase in glue weight. The same procedure was followed as in the second set of vertical experiments. 20 trials were attempted for each prototype.

Prototypes 2A, 2B, 2C and 3B all failed to hold the 2 balls vertically and were thus excluded from the results. Tables 5 to 7 show the results.

TABLE 5

| Current | | |
|---|---|---|
| Prototype | Mean (A) | Std. Dev. |
| 3A | 1.66 | 0.43 |
| 3B | n/a | n/a |
| 3C | 0.76 | 0.48 |
| 4A | 0.73 | 0.42 |
| 4B | 1.18 | 0.67 |
| 4C | 1.66 | 0.49 |

TABLE 6

| Voltage | | |
|---|---|---|
| Prototype | Mean (V) | Std. Dev. |
| 2A | 0.31 | 0.21 |
| 2B | n/a | n/a |
| 2C | 0.64 | 0.18 |
| 3A | 0.54 | 0.33 |
| 3B | 0.76 | 0.48 |
| 3C | 1.17 | 0.36 |

TABLE 7

| Power | | |
|---|---|---|
| Prototype | Mean (W) | Std. Dev. |
| 2A | 1.13 | 0.52 |
| 2B | n/a | n/a |
| 2C | 0.33 | 0.38 |
| 3A | 0.53 | 0.51 |
| 3B | 1.20 | 1.22 |
| 3C | 2.12 | 1.20 |

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to an embodiment of FIGS. 1A-6B may be combinable with any element described in relation to an embodiment of FIGS. 7A to 8B.

The present invention may be embodied in other forms, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A delivery device configured for delivering a ferrofluid, the device comprising:
    a catheter having a lumen extending to a distal opening at a distal end of the catheter;
    a magnet coupled to the catheter at a distal section of the catheter such that the catheter is configured to deliver the ferrofluid past the magnet to a desired fluid treatment site, wherein the magnet provides a magnetic field having strength sufficient to hold a bolus of the ferrofluid at the desired treatment site; and
    an ejection mechanism configured to eject the ferrofluid from the magnet, wherein the ejection mechanism is located at the distal end of the catheter.

2. The device of claim 1, wherein the magnet is a permanent magnet.

3. The device of claim 2, wherein the magnet is a rare earth magnet.

4. The device of claim 1, wherein the magnet is a solenoid.

5. The device of claim 1, wherein the ejection mechanism is a plunger.

6. The device of claim 1, wherein the ejection mechanism is a disconnectable portion of the catheter.

7. The device of claim 1, wherein the magnet has a hollow core configured to enable passage of the ferrofluid through the hollow core to the distal end of the magnet.

8. The device of claim 7, wherein the catheter extends at least partially into the hollow core toward the distal end of the magnet.

9. The device of claim 8, wherein the distal section of the catheter includes a tapered section and an outer diameter of the catheter is substantially aligned with an outer diameter of the magnet.

10. The device of claim 1, wherein the magnet has a length within a range of 1 to 3 cm.

11. The device of claim 1, wherein, at least at a distal section of the device, the device has an inner diameter within a range of 0.5 to 2 mm.

12. The device of claim 1, wherein the magnet has an outer diameter within a range of 1.5 to 4 mm.

13. A method of delivering a ferrofluid to a targeted treatment site using the device of claim 1, the method comprising:
    positioning the magnet coupled to the distal end of the catheter near the targeted treatment site;
    delivering an amount of the ferrofluid through the catheter and the magnet to the targeted treatment site, wherein the amount of the ferrofluid passes through a portion of the catheter and the magnet simultaneously; and
    controlling a position of the ferrofluid using the magnetic field generated by the magnet.

14. The method of claim 13, wherein controlling the position of the ferrofluid includes maintaining the position of the ferrofluid until an adhesive in the ferrofluid has set.

15. The method of claim 14, wherein the adhesive is a ferroadhesive.

16. The method of claim 13, further comprising ejecting the ferrofluid from the portion of the catheter and the magnet.

17. The method of claim 13, wherein the magnet is a permanent magnet.

18. The method of claim 13, wherein controlling the position of the ferrofluid includes constantly applying the magnetic field generated by the magnet.

19. A delivery device configured for delivering a ferroadhesive to a targeted pathological fistula in order to occlude the fistula, the device comprising:
a catheter having a lumen extending to a distal opening at a distal end of the catheter; and
a magnet coupled to the catheter at a distal section of the catheter, the magnet having a bore that encompasses at least a portion of the catheter, wherein the magnet provides a magnetic field having strength sufficient to hold a bolus of the ferroadhesive at the targeted fistula until the ferroadhesive has set, wherein the catheter extends at least partially into a hollow core toward the distal end of the magnet.

20. A delivery device configured for delivering a ferrofluid, the device comprising:
a catheter having a lumen extending to a distal opening at a distal end of the catheter;
a magnet coupled to the catheter at a distal section of the catheter such that the catheter is configured to deliver the ferrofluid past the magnet toward a desired fluid treatment site; and
an ejection mechanism configured to eject the ferrofluid from the magnet, wherein the ejection mechanism is located at the distal end of the catheter.

* * * * *